United States Patent [19]
Viegas et al.

[11] Patent Number: 5,277,911
[45] Date of Patent: Jan. 11, 1994

[54] ABLATABLE MASK OF POLYOXYALKYLENE POLYMER AND IONIC POLYSACCHARIDE GEL FOR LASER REPROFILING OF THE CORNEA

[75] Inventors: Tacey X. Viegas; Lorraine E. Reeve, both of Ann Arbor; Raymond L. Henry, Grosse Pointe Woods, all of Mich.

[73] Assignee: Mediventures, Inc., Grosse Pointe Park, Mich.

[21] Appl. No.: 604,705

[22] Filed: Oct. 26, 1990

Related U.S. Application Data

[63] Continuation-in-part of Ser. No. 563,638, Aug. 7, 1990, Pat. No. 5,077,033.

[51] Int. Cl.$^5$ .................. A61F 9/04; A61B 6/10; A61K 9/10; A61K 47/44; A61K 47/36; A61K 47/38
[52] U.S. Cl. .................. 424/427; 424/486; 424/488; 514/772.1; 514/777; 514/779; 514/781; 514/944; 252/315.2; 252/315.3; 523/121; 523/137; 523/179; 525/405; 525/916; 606/5
[58] Field of Search .............. 424/427, 486, 488; 514/772.1, 777, 779, 781, 944; 252/315.2, 315.3; 523/121, 137, 179; 525/405, 916; 606/5; 524/916; 340/796

[56] References Cited

U.S. PATENT DOCUMENTS

| | | | |
|---|---|---|---|
| 2,688,586 | 9/1954 | Ebeal et al. | 167/84 |
| 3,947,250 | 3/1976 | Pollack | 935/7 |
| 4,125,608 | 11/1978 | Pellico | 424/180 |
| 4,391,799 | 7/1983 | Mason, Jr. et al. | 424/132 |
| 4,393,048 | 7/1983 | Mason, Jr. et al. | 424/132 |
| 4,401,456 | 8/1983 | Lumnick, Jr. | 71/88 |
| 4,613,497 | 9/1986 | Chavrin | 424/44 |
| 4,856,513 | 8/1989 | Muller | 128/303.1 |
| 4,879,062 | 11/1989 | Moore | 514/789 |
| 4,911,926 | 3/1990 | Henry | 424/426 |
| 4,917,886 | 4/1990 | Asche et al. | 424/81 |
| 4,948,575 | 8/1990 | Cole et al. | 424/44 |

OTHER PUBLICATIONS

Journal of Cataract Refractive surgery, vol. 14 May 1988, pp. 312-316.

*Primary Examiner*—Edward Webman
*Attorney, Agent, or Firm*—Dykema Gossett

[57] ABSTRACT

Balanced pH, thermo-irreversible polyoxyalkylene polymer and ionic polysaccharide gels are ideal materials for use as an ablatable mask or coating over the cornea of the eye of a mammal during excimer laser keratectomy. The depth and smoothness of the ablated corneal surface can be controlled by molding the desired surface curvature into the mask surface using a contact lens as a mold which is pressed onto the gel surface coating the cornea.

45 Claims, 1 Drawing Sheet

RESISTANCE TO PENETRATION OF POLOXAMER-ALGINATE GEL vs. TEMPERATURE arrow denotes point of introduction of Calcium ions

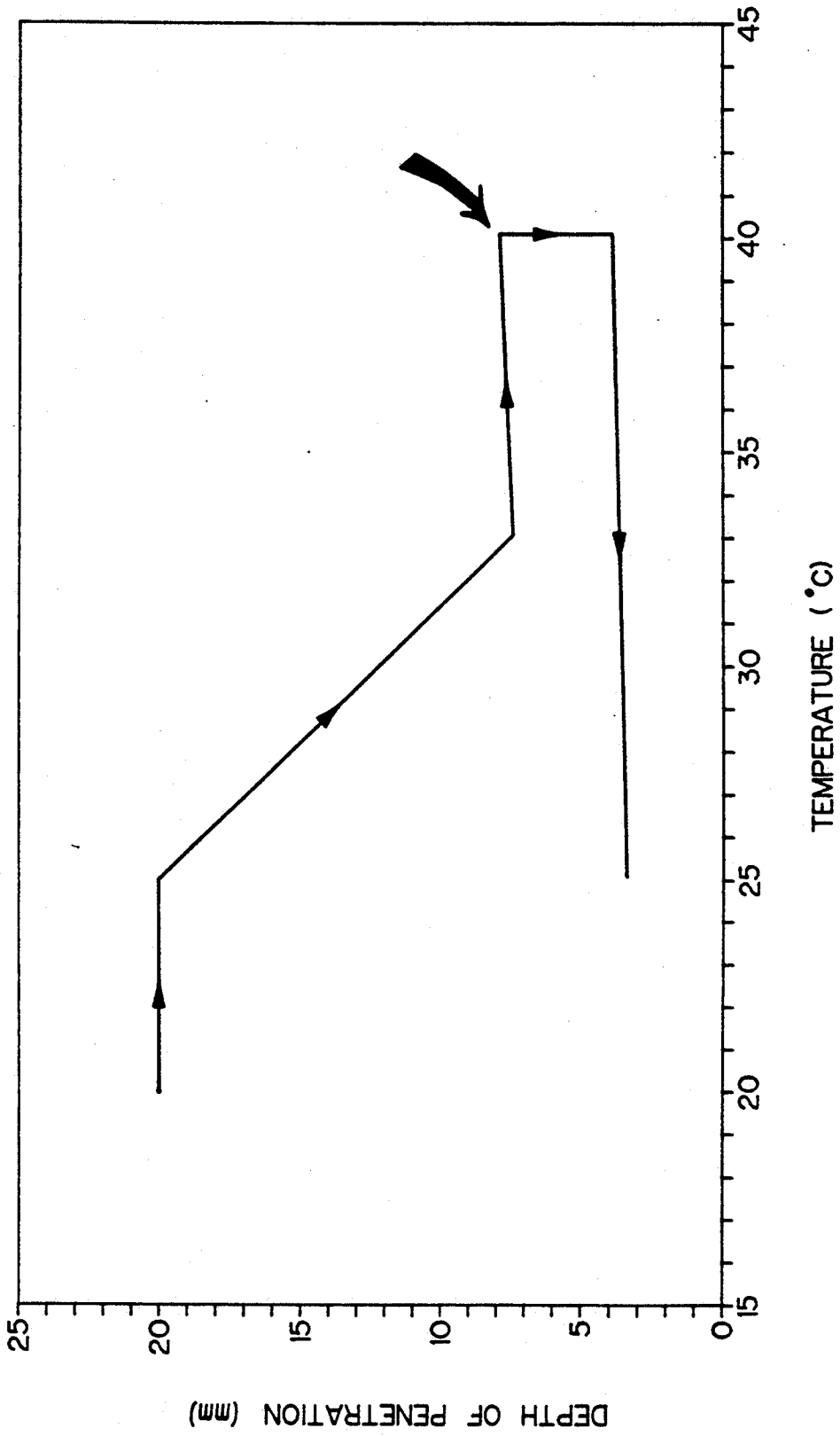

ABLATABLE MASK OF POLYOXYALKYLENE POLYMER AND IONIC POLYSACCHARIDE GEL FOR LASER REPROFILING OF THE CORNEA

This is a continuation-in-part of copending application(s) Ser. No. 07/563,638 filed on Aug. 7, 1990, now U.S. Pat. No. 5,077,033.

BACKGROUND OF THE INVENTION

1. Field of the Invention

This invention relates to surgical correction of corneal astigmatism, myopia, and hyperopia and a corneal contact mask utilized to control the delivery of the light from an excimer laser.

2. Description of the Prior Art

Refractive surgery has been promoted in the United States and Russia over the past few years but its acceptance has been limited because of the poor predictability of the final optical results which include a resulting glare from incisions that encroach upon the optical zone. Techniques that rely upon the surgical production of corneal incisions have yielded inconsistent results because these surgical incisions in the cornea have been found to vary considerably in depth and length.

Laser keratectomy has been shown to be capable of yielding a more accurately controlled depth of corneal excision since each individual laser pulse excises a specific amount (0.2 to 1.0 mm) of corneal tissue. Accordingly, the depth of excised tissue is in theory uniform and predictable, provided that the energy distribution is homogeneous across the laser beam. Since the primary locus of astigmatism is in the cornea, surgical intervention for astigmatism is more important than for the correction of other refractive errors, especially since spectacle or contact lens correction is of limited value in compensating for large astigmatic errors.

The excimer laser was introduced to ophthalmology in 1983 (Trokel, S., et al, "Excimer surgery of the cornea," *Am. J. Ophthalmol.* 96: 710–715, 1983). The depth of incision with short intense pulses permitted great precision to be achieved in tests on freshly enucleated cow eyes. The photochemical laser-tissue interaction is not thermal, permitting direct breaks of organic molecular bonds without involving optical breakdown in adjacent tissue. Early experimental results in rabbits revealed problems of (1) corneal stromal swelling, probably in response to disturbed water relationships due to compromise of the epithelial barrier and severing of the lamellae and (2) rearrangement of endothelial cells resulting from loss of contact inhibition (Marshall, J., et al, "An ultrastructural study of corneal incisions induced by an excimer laser at 193 nm", *Ophthalmology* 92: 749–758, 1985). Experiments with freshly enucleated human eyes indicated that flattening obtained by excimer laser ablation correlated with results of clinical scalpel radial keratotomy, but evaluation of the effects on wound healing and possible damage to adjacent structures was not addressed (Cotliar, A. M., et al, "Excimer laser radial keratotomy," *Ophthalmology* 92: 206–208, 1985). It was, however, suggested that this laser may become very useful in applications including penetrating and lamellar keratoplasty, keratomileusis, and epikeratophakia. Control of the area and depth of pulses using photolithographed masks resulted in ability to produce narrow cuts (20 μm) and at depths depending on pulse number (Puliafito, C. A., et al, "Excimer laser ablation of the cornea and lens", *Ophthalmology* 92: 741–748, 1985). These controlled ablations had only very narrow bands of destruction at the adjacent edges. These studies led to the quantitation of laser ablation (Krueger, R. R. and S. L. Trokel, "Quantitation of corneal ablation by ultraviolet laser light", *Arch. Ophthalmol.* 103: 1741–1742, 1985). Excimer far UV radiation can be controlled to produce minimal adjacent tissue damage providing the angle and depth can be precisely controlled. The remaining problem of effects on healing could then be addressed.

Comparison of 193 nm and 248 nm ablation of precise disc sizes on plastic surfaces, and on rabbit and monkey corneas was undertaken by early workers in the field (Marshall, J., et al, "Photoablative reprofiling of the cornea using an excimer laser: Photorefractive keratectomy", *Lasers in Ophthalmol.* 1: 21–48, 1986). Properly controlled, healing was not impaired. It was evident, however, that irregularities in final surface contour were due to (1) diffraction of the rays, (2) surface impurities or debris in the target zone, and (3) movement of the target between laser pulses. Initial inhomogeneity in or on the surface results in a high resistance site to the ablation process and shields the underlying tissue.

Ablations applicable to myopic correction have been attained in human eye bank eyes of up to 7.5 mm in diameter using a rotating beam delivery system (Hanna, K. D., et al, "Excimer laser keratectomy for myopia with a rotating-slit delivery system", *Arch. Ophthalmol.* 106:245–250, 1988). Excimer laser ablation appears to be highly applicable to correction of astigmatism (Seiler, T., et al, "Excimer laser keratectomy for correction of astigmatism", *Am. J. Ophthalmol.* 105: 177–124, 1988). These investigators observed that corneal thickness increases peripherally and the laser beam is not perpendicular to the surface at the point of irradiance.

Wound healing was assessed in rabbits following excimer laser surface ablation (Hanna, K. D., et al, "Corneal stromal wound healing in rabbits after 193 nm excimer laser surface ablation", Arch. Ophthalmol. 107: 895–901, 1989). Healing appeared to be excellent except when over 85% to 90% of the corneal thickness had been cut. Endothelial cell disruption, junction separation and individual cell dropout occurred with corneal haze development with the deeper cuts. A delivery system designed to deliver predictable depths of cut is, therefore, essential. Similar findings were reported in studies on human blind eyes (Taylor, D. M., et al, "Human excimer laser lamellar Keratectomy", *Ophthalmology* 96: 654–664, 1989). Attention was directed to the challenges of improved procedures and equipment, the problems of individual variation, and the control of biologic responses to trauma before excimer laser lamellar keratectomy could become a clinically useful means of correcting refractive errors. In living monkey eyes, it was concluded that mild, typical wound healing occurred after excimer laser keratomileusis (Fantes, F. E., et al, "Wound healing after excimer laser keratomileusis [photorefractive keratectomy] in monkeys", *Arch. Ophthalmol.* 108: 665–675, 1990). All corneas were epithelialized by 7 days. By 6 weeks, mild to moderate haze was apparent with clearing by 6 to 9 months. The epithelium was thickened at 21 days after ablation, but returned to normal by 3 months. Subepithelial fibroblasts were three times the density of normal keratocytes, but returned to nearly normal numbers by 9 months. One conclusion reached was that control of the contour and uniformity of the ablated surface is important for structural and biological responses of the cornea.

It has been observed that less haze and surface irregularities occur with tangential keratectomies of rabbit corneas in comparison to en face methods (Holme, R. J., et al, "A comparison of en face and tangential wide-area excimer surface ablation in the rabbit").

Another concern is the fluorescence spectra associated with ablation of corneal tissue. Wavelengths greater than 400 nm pass to the retina and may be phototoxic to the lens and to the retina. Studies designed to assess these concerns at ablative levels by 193 nm excimer lasers indicate that the fluorescence spectra can be attributed to the irradiated site rather than to luminous ablation products or laser-produced plasma. Thus, the phototoxic risk from the quantum yield of fluorescence from corneal ablation appears to be very slight (Tuft, S., et al, "Characterization of the fluorescence spectra produced by excimer laser irradiation of the cornea", *Invest. Ophthalmol. Visual Sci.* 31: 1512-1518, 1990).

Review of the literature clearly reveals that far UV vaporization (ablation with an excimer laser at 193 nm, for example) is a feasible means to sculpture or reprofile the cornea to correct nearsightedness, farsightedness, astigmatism, corneal scars, corneal densities, etc. The healing appears to parallel or to be equal to healing after scalpel intervention, providing the proper guidelines for pulsing and duration are followed. There remains a need to control the contour and uniformity of the ablated surface. Such control will reduce the adverse structural and biological response of the cornea and insure that a desired corrective change results.

The use of a mask of nearly identical optical density to the cornea that can be preformed on the surface of cornea so as to provide a smooth surface of exact contour would solve many of the problems still remaining which thus far have prevented precise control of laser beam keratotomy. Such a mask would be required to withstand exposure to moist gases directed tangentially to the corneal surface throughout the duration of exposure to the laser to remove ablated debris. The modulation of the beam energy distribution of the laser in a controlled fashion should also be provided by such a corneal mask. The use of a smooth ablatable mask having a known contour and having the density of the cornea would aid in insuring accurate direction and depth of a tangential cut utilizing a laser beam. The ablatable mask of the invention provides such advantages.

In "Pluronic Polyol, a Potential Alloplastic Keratorefractive Material", *Journal of Cataract Refractive Surgery*, Vol 14, May, 1988, Kim et al disclose the use of a polyol sold under the trademark PLURONIC® which is described as prepared by condensating propylene oxide on a propylene glycol nucleus followed by the condensating ethylene oxide onto both ends of the poly(oxypropylene) base. These polymers were evaluated as a potential material for alloplastic keratorefractive surgery in which the material in a liquid state was injected into a surgically prepared axial 7 mm mid-stromal corneal bed in rabbits. Post-operative follow-up over a period of three months indicated that the material was well tolerated by the cornea and provided refractive flattening of the cornea so as to obtain about 3 diopters change.

In U.S. Pat. No. 4,188,373, PLURONIC polyols are disclosed as forming aqueous compositions which are liquids when cool and gel upon heating. Adjusting the concentration of the polymer provides the desired sol-gel transition temperature, that is, the lower the concentration of polymer, the higher the sol-gel transition temperature, after crossing a critical concentration minimum, below which a gel will not form. Other polyoxyalkylene gel compositions are disclosed in U.S. Pat. Nos. 4,810,503 and 4,879,109.

Ionic polysaccharides have been used in the application of drugs by controlled release. Such ionic polysaccharides as chitosan or sodium alginate are disclosed as useful in providing spherical agglomerates of water-insoluble drugs in the *Journal of Pharmaceutical Sciences*, volume 78, number 11, November 1989, Bodmeier et al. Alginates have also been used as a depot substance in active immunization, as disclosed in the *Journal of Pathology and Bacteriology*, volume 77, (1959), C. R. Amies. Calcium alginate gel formulations have also found use as a matrix material for the controlled release of herbicides, as disclosed in the *Journal of Controlled Release*, 3 (1986) pages 229-233, Pfister et al. Alginates have also been used to form hydrogel foam wound dressings, as disclosed in U.S. Pat. No. 4,948,575.

SUMMARY OF THE INVENTION

Ablatable gel compositions and a process for excimer laser ablation for myopic vision correction are disclosed. In the process of the invention, an ablatable gel coating is formed upon the cornea, said coating having a known and precise curvature which functions to guide the depth of excision of an excimer laser so that a precise and predictable end result curvature can be obtained on the cornea. Use of the ablatable gel of the invention is advantageous over prior art laser ablation processes which result in an uneven excised depth when the surface of the cornea has an uneven curvature. The surface curvature of the cornea is rendered uneven by scarring or even the presence of an aqueous film of water varying in depth, such as produced by the presence of lacrimal tears.

The compositions in one embodiment of the invention provide a physiologically acceptable aqueous media which has a buffered pH and is osmotically balanced, preferably, so as to provide an isotonic mixture which is iso-osmotic with body fluids and has a pH similar to bodily fluids, such as lacrimal tears. The pH and osmotic pressure of lacrimal tears is about pH 7.4 and 290 mOsm/kg. In addition, the compositions are, optionally, sterilized so as to insure that the protective compositions of the invention do not provide a source of infection.

Polyphase systems are also useful and may contain non-aqueous solutes, non-aqueous solvents, and other non-aqueous additives. Homogeneous, polyphase systems can contain such additives as water insoluble high molecular weight fatty acids and alcohols, fixed oils, volatile oils and waxes, mono-, di-, and triglycerides, and synthetic, water insoluble polymers without altering the functionality of the system.

The compositions of the invention in one embodiment comprise aqueous mixtures of a polyoxyalkylene polymer and an ionic polysaccharide, optionally containing a latent counter-ion to gel the polysaccharide upon release of the counter-ion and to render the gelled mixture thermally irreversible so that it remains a gel upon cooling and thus is rendered durable at ambient temperature. The counter-ion can be microencapsulated in a heat sensitive medium, for instance, the walls of the microcapsule can be made of mono-, di-, or triglycerides or other natural or synthetic heat sensitive polymer medium. Alternatively, ion exchange resins can be incorporated in the compositions of the invention so as to release the desired counter-ion upon contact with an environment opposite in pH to the pH of the ion exchange resin. The aqueous mixture can be delivered to the cornea of the mammalian body as a low viscosity liquid at ambient temperatures which, upon contact with the higher temperature mammalian body, forms a semisolid gel having a very high viscosity. Release of the counter-ion further strengthens the gel and renders it irreversible upon cooling to ambient temperature.

Alternatively, a two part system can be used in which the counter-ion can be separately applied to the semisolid gel formed by the polyoxyalkylene polymer upon contact with the cornea. This further strengthens the gel and renders it irreversible upon cooling.

The counter-ion can be conveniently applied to the concave surface of a contact lens which is then applied over the aqueous mixture of a polyoxyalkylene polymer and an ionic polysaccharide. This serves to strengthen the gel and renders the gel irreversible upon cooling. At the same time, the contour of the concave surface of the contact lens is imparted to the gel, thus rendering the surface of the gel of uniform contour subsequent to removal of the contact lens.

Because the preferred compositions of the invention are low viscosity liquids at ambient temperatures, they easily coat the cornea insuring maximum contact between exposed tissue and the compositions of the invention. The gel compositions of the invention can be peeled away subsequent to application to the cornea, if desired.

A wide variety of polyoxyalkylene polymers are suitable for the preparation of the pharmaceutical compositions of the invention. Generally, it is necessary to adjust the polymer concentration in aqueous solution so as to obtain the desired sol-gel transition temperature in order that the compositions can be provided as low viscosity liquids at ambient temperature, yet form semisolid gels at mammalian body temperatures. In addition to controlling the concentration of the polymer, other suitable excipients can be added so as to provide the desired pH and isotonic, iso-osmotic properties.

The useful polymers which provide the sol-gel characteristics of the pharmaceutical compositions of the invention are, preferably, polyoxyalkylene block copolymers.

The ionic polysaccharides are natural polymers such as chitosan or alginates. Aqueous solutions of alginate ionic polysaccharides form gels upon contact with aqueous solutions of counter-ions such as calcium, strontium, aluminum, etc. Aqueous solutions of chitosan form gels upon contact with a metal tripolyphosphate counter-ion. The discovery forming the basis of this invention is that when ionic polysaccharides are present in aqueous solutions in admixture with certain polyoxyalkylene block copolymers and a counter-ion, that such mixtures form thermally-irreversible gels instead of the thermo-reversible gels known to form with aqueous solutions of certain polyoxyalkylene block copolymers. The thermo-reversible gels of the prior art are insufficiently firm and resistant to softening for use as ablatable masks.

DESCRIPTION OF THE DRAWING

The drawing provides a curve showing the penetration, as measured by a Precision Universal Penetrometer, of a 20 mm thickness aqueous gel comprising poloxamer 407 and an alginate prepared in accordance with the procedure of Example 1. The scale at the left side of the plot indicates the depth of penetration, while the scale on the bottom of the plot indicates the temperature of the composition when tested. The arrow in the plot indicates the point at which an aqueous solution of calcium ions at a concentration of 0.137 molar is made to contact the gelled poloxamer 407/alginate solution so as to render thermally irreversible the gelled mixture and prevent it from becoming fluid at ambient temperature.

DETAILED DESCRIPTION OF THE INVENTION

It has been found that aqueous mixtures containing a polyoxyalkylene block copolymer, which have the unique feature of being liquid at ambient temperatures and transitioning at mammalian body temperatures to a semisolid gel, can be rendered thermally irreversible (no longer a liquid at ambient temperature) and resistant to shear thinning. Upon contacting the mixture with a counter-ion, the polyoxyalkylene polymer aqueous gel becomes more resistant to penetration and less sticky. The inclusion of an ionic polysaccharide in admixture with the polyoxyalkylene polymer results, in one embodiment of the invention, in an aqueous gel at mammalian body temperature that is rendered more firm and thermally irreversible.

In use, the block copolymer and alginate, aqueous compositions of the invention are poured onto the corneal surface. Preferably, a thermally reversible gel forms in situ. Thereafter, in one embodiment of the process of the invention, a contact lens having an aqueous coating of a di- or trivalent metal salt on the concave surface thereof is placed over the thermally reversible gel which covers the corneal surface. The thermally reversible gel is quickly converted to a thermally irreversible gel upon contact with the di- or trivalent metal salt. Thereafter, the contact lens is removed and the corneal surface is suitable for laser ablation to correct myopia. It is desirable to provide such ablative corneal mask gel compositions having an aqueous carrier, said compositions having a pH and osmotic pressure which match those of bodily fluids. Optionally, the compositions of the invention can be provided in a sterile condition.

The block copolymer component of the compositions of the invention comprise: at least one polyoxyalkylene block copolymer of the formula

$$Y[(A)_n-E-H]_x \qquad (I)$$

wherein A is a polyoxyalkylene moiety having an oxygen/carbon atom ratio of less than 0.5, x is at least 2, Y is derived from water or an organic compound containing x reactive hydrogen atoms, E is a polyoxyalkylene moiety constituting at least about 60% by weight of the copolymer, n has a value such that the average molecular weight of A is at least about 500 to about 900" and replace it with "n has a value such that the minimum molecular weight of A is between about 500 and about 900, as determined by the hydroxyl number of a hydrophobe base intermediate,

$$Y[(A)_n-H]_x \qquad (II)$$

and the total average molecular weight of the copolymer is at least about 5,000.

Generally, the polyoxybutylene-based block copolymers useful in the compositions of the invention are prepared by first condensing 1,2 butylene oxide with a water soluble organic compound initiator containing 1 to about 6 carbon atoms, such as, 1,4 butylene glycol or propylene glycol and at least 2 reactive hydrogen atoms to prepare a polyoxyalkylene polymer hydrophobe of at least about 500, preferably, at least about 1000, most preferably, at least about 1500 average molecular weight. Subsequently, the hydrophobe is capped with an ethylene oxide residue. Specific methods for preparing these compounds are described in U.S. Pat. No. 2,828,345 and British Patent No. 722,746, both of which are hereby incorporated by reference.

Useful polyoxybutylene based block copolymers conform to the following generic formula:

$$HO(C_2H_4O)_b(C_4H_8O)_a(C_2H_4O)_bH \quad (III)$$

wherein a and b are integers such that the hydrophobe base represented by $(C_4H_8O)_a$ has a molecular weight of at least about 500, preferably, at least about 1000 and most preferably, at least about 3000, as determined by hydroxyl number, the polyoxyethylene chain constituting at least about 60%, preferably, at least about 70% by weight of the copolymer and the copolymer having a total average molecular weight of at least about 5000, preferably, at least about 10,000, and most preferably, at least about 15,000.

The copolymer is characterized in that all the hydrophobic oxybutylene groups are present in chains bonded to an organic radical at the former site of a reactive hydrogen atom thereby constituting a polyoxybutylene base copolymer. The hydrophilic oxyethylene groups are used to cap the polyoxybutylene base polymer.

Polyoxyethylene-polyoxypropylene block copolymers which can be used to form aqueous gels can be represented by the following formula:

$$HO(C_2H_4O)_b(C_3H_6O)_a(C_2H_4O)_bH \quad (IV)$$

wherein a and b are integers such that the hydrophobe base represented by $(C_3H_6O)_a$ has a molecular weight of at least about 900, preferably, at least about 2500, most preferably, at least about 4000 average molecular weight, as determined by hydroxyl number; the polyoxyethylene chain constituting at least about 60%, preferably, at least about 70% by weight of the copolymer and the copolymer having a total average molecular weight of at least about 5000, preferably, at least about 10,000, and most preferably, at least about 15,000.

Polyoxyethylene-polyoxypropylene block copolymer adducts of ethylenediamine which can be used may be represented by the following formula:

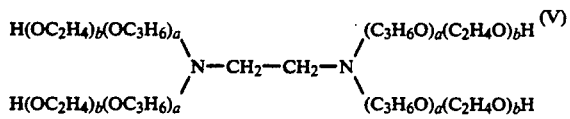

wherein a and b are integers such that the copolymer may have (1) a hydrophobe base molecular weight of at least about 2000, preferably, at least about 3000, and most preferably, at least about 4500, (2) a hydrophile content of at least about 60%, preferably, at least about 70% by weight, and (3) a total average molecular weight of at least about 5000, preferably, at least about 10,000, and most preferably, at least about 15,000.

The hydrophobe base of the copolymer of formula V is prepared by adding propylene oxide for reaction at the site of the four reactive hydrogen atoms on the amine groups of ethylenediamine. An ethylene oxide residue is used to cap the hydrophobe base. The hydrophile polyoxyethylene groups are controlled so as to constitute at least about 60%, preferably, at least about 70% by weight, and most preferably, at least about 80% by weight of the copolymer.

The procedure used to prepare aqueous solutions which form gels of the polyoxyalkylene block copolymers is well known. Either a hot or cold process for forming the solutions can be used. A cold technique involves the steps of dissolving the polyoxyalkylene block copolymer at a temperature of about 5° to about 10° C. in water. When solution is complete the system is brought to room temperature whereupon it forms a gel. If the hot process of forming the gel is used the polymer is added to water heated to a temperature of about 75° C. to about 85° C. with slow stirring until a clear homogeneous solution is obtained Upon cooling, a clear gel is formed. Block copolymer gels containing polyoxybutylene hydrophobes must be prepared by the above hot process, since these will not liquify at low temperatures.

As used herein, the term "gel" is defined as a solid or semisolid colloid containing a certain quantity of water. The colloidal solution with water is often called a "hydrosol".

The organic compound initiator which is utilized in the process for the preparation of the polyoxyalkylene block copolymers generally is water or an organic compound and can contain a plurality of reactive hydrogen atoms. Preferably, Y in formulas I and II above is defined as derived from a water soluble organic compound having 1 to about 6 carbon atoms and containing x reactive hydrogen atoms where x has a value generally, of at least 1, preferably, a value of at least 2. Falling within the scope of the compounds from which Y is derived from water soluble organic compounds having at least two reactive hydrogen atoms are water soluble organic compounds such as propylene glycol, glycerin, pentaerythritol, trimethylolpropane, ethylenediamine, and mixtures thereof and the like.

The oxypropylene chains can optionally contain small amounts of at least one of oxyethylene or oxybutylene groups. Oxyethylene chains can optionally contain small amounts of at least one of oxypropylene or oxybutylene groups. Oxybutylene chains can optionally contain small amounts of at least one of oxyethylene or oxypropylene groups. The physical form of the polyoxyalkylene block copolymers can be a viscous liquid, a paste, or a solid granular material depending upon the molecular weight of the polymer. Useful polyoxyalkylene block copolymers generally have a total average molecular weight of about 5,000 to about 50,000, preferably, about 5,000 to about 35,000 and most preferably, about 10,000 to about 25,000.

In addition to those polyoxyalkylene block copolymers referred to above, which are suitable in the formation of the pharmaceutical compositions of the invention, other polyoxyalkylene polymers which form gels at low concentrations in water are suitable. One such polymer is described in U.S. Pat. No. 4,810,503, incorporated herein by reference. These polymers are prepared by capping conventional polyether polyols with an alpha-olefin epoxide having an average of about 20 to about 45 carbon atoms, or mixtures thereof. Aqueous solutions of these polymers gel in combination with surfactants, which can be ionic or nonionic. The combination of the capped polyether polymers and the surfactants provide aqueous gels at low concentrations of the capped polymer and surfactant, which generally do not exceed 10% by weight total. Detailed methods of preparing these aqueous gels are disclosed in U.S. Pat. No. 4,810,503. Preparation of said aqueous gels is generally described below. Preferred surfactants for use in preparing these gels are also disclosed in said patent.

A conventional copolymer polyether polyol is prepared by preparing block or heteric intermediate polymers of ethylene oxide and at least one lower alkylene oxide having 3 to 4 carbon atoms as intermediates. These are then capped with the alpha-olefin epoxide to prepare the polymers. Ethylene oxide homopolymers capped with said alpha-olefin oxides are also useful as intermediates.

The heteric copolymer intermediate is prepared by mixing ethylene oxide and at least one lower alkylene oxide having 3 to 4 carbon atoms with a low molecular weight active hydrogen-containing compound initiator having at least two active hydrogens and preferably, 2 to 6 active hydrogen atoms such as a polyhydric alcohol, containing from 2 to 10 carbon atoms and from 2 to 6 hydroxyl groups, heating said mixture to a temperature in the range of about 50° C. to 150° C., preferably from 80° C. to 130° C., under an inert gas pressure preferably from about 30 psig to 90 psig.

A block copolymer intermediate is prepared by reacting either the ethylene oxide or said alkylene oxide having 3 to 4 carbon atoms with said active hydrogen-containing compound followed by reaction with the other alkylene oxide.

The ethylene oxide and the alkylene oxides having from 3 to 4 carbon atoms are used in said intermediates in amounts so that the resulting polyether product will contain at least 10 percent by weight, preferably about 70 percent to about 90 percent by weight, ethylene oxide residue. The ethylene oxide homopolymer intermediate is prepared by reacting ethylene oxide with said active hydrogen-containing compound. The reaction conditions for preparing the block copolymer and ethylene oxide homopolymer intermediates are similar to those for the heteric copolymer intermediate. The temperature and pressure are maintained in the above ranges for a period of about one hour to ten hours, preferably one to three hours.

The alpha-olefin oxides which are utilized to modify the conventional polyether intermediate of the prior art are those oxides and the commercially available mixtures thereof generally containing an average of about 20 to 45, preferably about 20 to 30, carbon atoms. The amount of alpha-olefin required to obtain the more efficient capped polyethers is generally about 0.3 to 10 percent, preferably about 4 to 8 percent, of the total weight of the polyethers.

Since the preparation of heteric and block copolymers of alkylene oxides and ethylene oxide homopolymers are well known in the art, further description of the preparation of said polymers is unnecessary. Further details of the preparation of heteric copolymers of lower alkylene oxide can be obtained in U.S. Pat. No. 3,829,506, incorporated herein by reference. Further information on the preparation of block copolymers of lower alkylene oxides can be obtained in U.S. Pat Nos. 3,535,307; 3,036,118; 2,979,578; 2,677,700; and 2,675,619 incorporated herein by reference.

The surfactants may be ionic or nonionic and many surfactants and types of surfactants may be employed. While all surfactants may not be effective in the preparation of the isotonic gels of the instant invention, the fact that many are effective makes it a simple matter for one skilled in the art to select such surfactant with a minimum of trial and error.

The amounts of capped polyether polymer and surfactant may be as little as 1.0 percent by weight or less of each depending on the type and amount of the other component. There appears to be no maximum amount of either component than that dictated by economic considerations. However, the total amount of capped polymer and surfactant would generally not exceed 10 percent by weight.

The ionic polysaccharides found useful in the present invention are hydrophilic colloidal materials and include the natural gums such as alginate gums, i.e., the ammonium and alkali metal salts of alginic acid and mixtures thereof as well as chitosan, which is a common name for the deacetylated form of chitin. Chitin is a natural product comprising poly-(N-acetyl-D-glucosamine). The alginates are available as dry powders from Protan, Inc., Commack, New York and from Kelco Company, San Diego, Calif.

Generally, the alginates can be any of the water-soluble alginates including the alkali metal alginates, such as sodium, potassium, lithium, rubidium and cesium salts of alginic acid, as well as the ammonium salt, as well as the soluble alginates of an organic base such as mono-, di-, or triethanolamine, aniline and the like. Generally, about 0.2% to about 2.5% by weight and, preferably, about 0.5% to about 1.5% by weight of alginate or chitosan ionic polysaccharides, based upon the total weight of the composition, are used to obtain the thermo-irreversible compositions of the invention. In general, the drug delivery composition of the invention will contain about 0.01% to about 60% by weight of medicament or pharmaceutical, about 10% to about 50% by weight of the polyoxyalkylene block copolymer, and about 80% to about 20% by weight of water together with the above amounts of ionic polysaccharide. In special situations, these amounts may be varied to increase or decrease the dosage or gel properties.

Useful counter-ions for thermo-irreversibly gelling the alginate ionic polysaccharide in combination with the polyoxyalkylene polymer compositions of the invention are cationic gelling agents, preferably, comprising a divalent or trivalent cation. Useful divalent cations include the alkaline earth metals, preferably, selected from the group consisting of calcium and strontium. Useful trivalent cations include aluminum. The most preferred counter-ions for gelling an alginate are contained in ionic compounds selected from pharmaceutically-acceptable gluconates, fluorides, citrates, phosphates, tartrates, sulfates, acetates, borates, chlorides, and the like having alkaline earth metal cations such as calcium and strontium. Especially perferred counter-ion containing inorganic salts for use as ionic polysaccharide gelling agents include such inorganic salts as the chloride salts, such as strontium chloride, calcium chloride, and mixtures thereof. Generally, a molar ratio of counter-ion to chitosan or alginate of about 1:1 to about 10:1, preferably, about 2:1 to about 5:1, and, most preferably, about 3:1 to about 5:1 is used to render the compositions of the invention thermally-irreversibly gelled.

While the counter-ion, such as calcium or other divalent ions may be obtained by contact with bodily fluids, such as lacrimal tears, it is preferred that the counter-ion in latent form be added to the alginate ionic polysaccharide and polyoxyalkylene polymer compositions of the invention. Alternatively, it is preferred that the counter-ion be added to the alginate ionic polysaccharide and polyoxyalkylene polymer compositions of the invention utilizing a two part system in which the counter-ion part is topically applied to the polyoxyalkylene polymer part. For instance, the counter-ion can be applied to the concave surface of a hard or soft contact lens as an aqueous solution of a salt of a divalent or trivalent metal, as previously described. The contact lens is then applied over a coating of an aqueous solution of the thermally reversible gel polyoxyalkylene compositions of the invention subsequent to the topical application of such compositions to the cornea.

Incorporation of the counter-ion in a latent form together with the alginate ionic polysaccharide and polyoxyalkylene polymer compositions of the invention may be accomplished by either encapsulating an aqueous solution of one of the counter-ion gelling agents, previously described above or by the incorporation of the counter-ion gelling agent into a matrix which provides for the controlled, slow-release of the gelling agent. For instance, the gelatin-encapsulated controlled-release compositions disclosed in U.S. Pat. No. 4,795,642, incorporated herein by reference, disclose the preparation of a gelatin shell encapsulating a controlled-release formulation in which the gelatin composition includes calcium chloride as the gelling agent. Alternatively, the counter-ion can be incorporated as an aqueous solution of a cationic gelling agent encapsulated in a vesicle composed, for instance, of alpha-tocopherol, as disclosed in U.S. Pat. No. 4,861,580, incorporated herein by reference.

Generally, aqueous solutions of chitosan can be gelled with multivalent anion gelling agents, preferably, comprising a metal polyphosphate, such as an alkali metal or ammonium polyphosphates, pyrophosphates, or metaphosphates. Representative metaphosphate, pyrophosphate, and polyphosphate gelling agents include sodium and potassium, polyphosphates, sodium and potassium pyrophosphates, sodium and potassium metaphosphates, and sodium and ammonium (mono-, di-, tri-) phosphates.

The corneal mask compositions of the invention are an improvement over the prior art thermo-reversible gels based upon polyoxyalkylene polymers, in that the compositions provide greater gel strength because they are more resistant to shear thinning and are characterized as thermally-irreversible. These advantages are obtained by the incorporation of an ionic polysaccharide in admixture with a polyalkylene polymer. They can be optimized for optimum physiological tolerance in the eye by formulating the compositions so as to have a neutral pH and isotonic characteristics. These former advantages are obtained by the incorporation of an ionic polysaccharide in admixture with a polyalkylene polymer. By matching the osmolality and pH of the laser ablatable corneal mask compositions of the invention to those of the lacrimal fluid of the eye, it is possible to eliminate burning or other discomfort upon application of the corneal mask of the invention to the eye. The higher gel strength compositions upon contact with a counter-ion allow retention of the gel as an in situ formed corneal mask for long intervals.

If desired, the laser ablatable corneal mask of the invention may also contain preservatives, cosolvents, suspending agents, viscosity enhancing agents, ionic-strength and osmolality adjustors and other excipients in addition to the polyoxyalkylene polymer and ionic polysaccharide. Suitable water soluble preservatives which may be employed are sodium bisulfite, sodium thiosulfate, ascorbate, benzalkonium chloride, chlorobutanol, thimerosal, phenylmercuric borate, parabens, benzyl alcohol phenylethanol and others. These agents may be present, generally, in amounts of about 0.001% to about 5% by weight and, preferably, in the amount of about 0.01 to about 2% by weight.

Suitable water soluble buffering agents are alkali or alkaline earth metal carbonates, phosphates, bicarbonates, citrates, borates, acetates, succinates and the like, such as sodium phosphate, citrate, borate, acetate, bicarbonate, carbonate and tromethamine (TRIS). These agents are present in amounts sufficient to maintain the pH of the system at $7.4 \pm 0.2$ and preferably, 7.4. As such, the buffering agent can be present in an amount of as much as 5% on a weight basis of the total composition.

Representative buffering agents or salts useful in maintaining the pH at about $7.4 \pm 0.2$ are alkali or alkali earth carbonates, chlorides, sulfates, phosphates, bicarbonates, citrates, borates, acetates and succinates. Representative preservatives are sodium bisulfite, sodium thiosulfate, ascorbate, benzalkonium chloride, chlorobutanol, thimerosal, phenylmercuric borate, parabens, benzyl alcohol and phenylethanol.

The preparation of the laser ablatable corneal mask compositions of the invention are described below. The Examples which follow are prepared in accordance with the following preparation procedure. Since the polyoxyalkylenes dissolve more completely at reduced temperatures, the preferred methods of solubilization are to add the required amount of polymer to the amount of water to be used. Generally after wetting the polymer by shaking, the mixture is capped and placed in a cold chamber or in a thermostatic container at about 0° C. to 10° C. in order to dissolve the polymer. The mixture can be stirred or shaken to bring about a more rapid solution of the polymer. The various additives, such as buffers, salts, and preservatives, can subsequently be added and dissolved. The desired pH of $7.4 \pm 0.2$ is obtained by the addition of appropriate buffering agents.

The following Examples illustrate the various aspects of the invention but are not intended to limit its scope. Where not otherwise specified throughout this specification and claims, temperatures are given in degrees centigrade and parts, percentages, and proportions are by weight.

EXAMPLE 1

This Example describes a composition of the invention for opthalmic use as a laser ablatable corneal mask. The composition prepared was characterized as iso-osmotic, sterile, and having a pH of $7.4 \pm 0.2$. An aqueous solution was made of a polyoxyethylene-polyoxypropylene block copolymer having the structure generically shown above as Formula IV and having a polyoxypropylene hydrophobe base average molecular weight of about 4000, a total average molecular weight of about 11,500, and containing oxyethylene groups in the amount of about 70% by weight of the total weight of copolymer. This copolymer (Formula VI below) is sold under the trademark PLURONIC® F-127 (also known as Poloxamer 407) by the BASF Corporation, Parsippany, New Jersey. A solution in TRIS hydrochloride buffer was made by dissolving said polymer and sodium alginate in cold (4° C.) buffer to give a concentration of 19% by weight polyoxyalkylene and 1% by weight sodium alginate. More specific solution procedures are described in "Artificial Skin I Preparation and Properties of PLURONIC F-127 Gels For Treatment of Burns", *Journal of Biomedical Material Research* 6, 527, 1972, incorporated herein by reference. The block copolymer has the formula:

(VI)

This formulation forms the basis for the Figure in which the curve shows the penetration of a 20 mm thickness aqueous gel at various temperatures. After contact of the gel with calcium ions, as indicated by the vertical line at 40° C., the gel strength is not reduced or the composition rendered fluid by lowering the temperature to 25° C. The UV absorption spectra of PLURONIC F-127 has an absorption maxima at 192.5±1 nm which corresponds to the argon fluoride laser wavelength, thus, suggesting that there will be a strong interaction of this material with the laser light from an argon fluoride laser.

EXAMPLES 2 and 3

These examples describe pH balanced, thermo-sensitive aqueous systems which are suitable for forming a thermally reversible corneal contact lens in situ. Both examples will result in the formation of thermally irreversible systems upon exposure to an aqueous solution of 2% to 10% by weight calcium chloride. The formulations are:

| Ingredient | Example 2 | Example 3 |
| --- | --- | --- |
| | Percent by weight | |
| Poloxamer 407 (block, BHT free) | 16.0 | 16.0 |
| Sodium alginate | 1.0 | 1.0 |
| Boric acid-Borate Buffer pH 7.4 | 82.7 | — |
| Phosphate-Borate Buffer pH 7.4 | — | 82.7 |
| Glycerin | 0.3 | 0.3 |

The formulations are prepared by the "Hot Method", "BWC surfactants in gel cosmetics", I. R. Schmolka, *Cosmetics and Toiletries,* vol 92, July 1977, pages 77–79. The procedure is as follows:

1. The poloxamer blocks (BASF Corp) are melted at 65° C. in a water jacketed mixing bowl. The mixer used is a Stephan UMC$_5$ mixer-blender (Stephan Machinery, Columbus, Ohio).
2. A weighed amount of buffer is placed in a one liter beaker. Weighed amounts of Glycerin (JT Baker) and Sodium Alginate (Protonal SF120, Protan, Inc.) are added to dissolve and mix.
3. This solution is added to the molten poloxamer and mixed at 65° C. for 15 minutes in a nitrogen atmosphere.
4. The temperature is gradually dropped to 25° C. and then to 15° C. by the circulation of ice-cold water.
5. The final product is stored overnight at 4° C. in a glass beaker.
6. The next day the following tests were done and the results were as follows:

| Test | Example 2 | Example 3 |
| --- | --- | --- |
| 1. pH | 7.37 | 7.44 |
| 2. Osmolality in gelled state (calculated mOsm/kg) | 290 iso-osmotic | 350 hyperosmotic |
| 3. Solution-Gel Profile (Brookfield Viscometer) (10 rpm, at 33° C.) | strong gel 50,000 cps | weak gel 1000 cps |

EXAMPLES 4 and 5

Examples 2 and 3 are repeated substituting for poloxamer 407, 2% by weight of polymer #2, as described in U.S. Pat. No. 4,810,503 and 4% by weight of surfactant #1, as described therein. The balance of the percentage of Poloxamer 407 used in Examples 2 and 3 is made up with borate or phosphate-borate buffer, respectively. These formulations form soft gels at room temperature which are usefully stiffened upon exposure to a 2% to about 10% by weight aqueous solution of calcium chloride. Substantially similar pH and osmolality results are obtained.

EXAMPLE 6

Ion exchange resin beads sold under the tradename Duolite were treated so as to incorporate calcium by first treating a 30 gram sample of the ion exchange resin with a solution of 0.1 molar hydrochloric acid so as to allow for the exchange of protons for sodium. After three washings with 0.1 molar hydrochloric acid, the beads were washed with water and then washed twice with a 2% aqueous solution of calcium chloride. Each of the washing steps took place over a period of 16 hours (overnight). The beads were thereafter filtered and washed with water utilizing coarse filter paper and a Buchner glass filter assembly. The beads were then left overnight in a desiccator to dry. The dried beads of ion exchange resin which were obtained are utilized in the amount of 2 grams to fill a first compartment (close to the needle of the syringe) of a glass syringe utilized to apply liquids and dry materials. The syringe is sold under the tradename Hypak. Into the second compartment of the syringe, there is placed the solution of Example 2. Pushing the plunger of the syringe forward results in mixing the solution of Example 2 with the ion exchange beads. After 5 to 10 minutes subsequent to mixing, the mixture is expelled from the syringe. After an additional 15 minutes the expelled material forms a thermo-irreversible film on the substrate on which it is expelled.

EXAMPLE 7

This example describes the application of the solution of Example 2 to the cornea of a rabbit eye and the conversion of a thermally-reversible gel to a thermally-irreversible gel by the application of a 10% calcium chloride solution having a pH of 6.9. The calcium chloride solution is applied to the concave surface of a contact lens prior to contacting the surface of the gel formed upon the cornea of the rabbit eye utilizing the composition of Example 2. After applying the composition of Example 2 to the cornea of a rabbit placed under general anesthesia, it is found that a thermally-reversible gel forms upon contact with the cornea. Subsequently, a 10% aqueous solution of calcium chloride is applied to the concave surface of a hard contact lens and the contact lens is placed over the thermally-reversible gel coating the cornea of the rabbit eye. The time required for a thermally-reversible gel to convert to a thermally-irreversible gel is approximately 5 minutes. Thereafter, the contact lens is removed to expose a perfectly smooth and optically clear gelled surface of the composition of Example 2. Excimer laser keratectomy is thereafter performed utilizing an argon fluoride excimer laser (193 nm). Further details of excimer laser keratectomy process can be found in *Archives of Ophthalmology*, Vol. 106, February, 1988, entitled "Excimer Laser Keratectomy for Myopia with a Rotating-slit Delivery System", Hanna et al, incorporated herein by reference.

While this invention has been described with reference to certain specific embodiments, it will be recognized by those skilled in the art that many variations are possible without departing from the scope and spirit of the invention, and it will be understood that it is intended to cover all changes and modifications of the invention, disclosed herein for the purposes of illustration, which do not constitute departures from the spirit and scope of the invention.

The embodiments of the invention in which an exclusive property or privilege is claimed are defined as follows:

1. An ablatable corneal mask for use in excimer laser keratectomy for correction of myopia and hyperopia, said mask comprising a thermally irreversible, osmotically balanced aqueous gel, having a buffered pH, wherein said aqueous gel is the reaction product of a thermally reversible aqueous gel and a multivalent counter-ion, wherein said thermally reversible aqueous gel is a liquid at room temperature or below and a gel at mammalian body temperature, said thermally reversible aqueous gel containing (1) about 0.2% to about 2.5% by weight of an ionic polysaccharide;
   (2) about 10% to about 50% by weight of a polyoxyalkylene block copolymer of formula

   $$Y[(A)_n-E-H]_x \qquad (I)$$

wherein A is a polyoxyalkylene moiety having an oxygen/carbon atom ratio of less than 0.5, x is at least 2, Y is derived from water or an organic compound containing x reactive hydrogen atoms, E is a polyoxyethylene moiety constituting at least 60% by weight of the polyoxyalkylene block copolymer, n has a value such that the average molecular weight of A is at least about 500, as determined by the hydroxyl number of an intermediate of formula

   $$Y[(A)_n-H]_x \qquad (II)$$

and the total average molecular weight of the polyoxyalkylene block copolymer is at least about 5000; and
   (3) a pharmaceutically acceptable buffer sufficient to maintain the pH of said thermally reversible aqueous gel at a desired level;

wherein the muiltivalent counter-ion is capable of thermo-irreversibly gelling the ionic polysaccharide in the thermally reversible aqueous gel.

2. The mask of claim 1, wherein Y in said polyoxyalkylene block copolymer is derived from a water soluble organic compound having 1 to about 6 carbon atoms wherein the pH of said thermally reversible aqueous gel is maintained at 7.4±0.2, and the multivalent counter-ion is a divalent of trivalent counter-ion.

3. The mask of claim 2, wherein said polyoxyalkylene moiety is derived from an alkylene oxide selected from the group consisting of butylene oxide, propylene oxide, and mixtures thereof and Y is derived from an organic compound selected from the group consisting of propylene glycol, glycerin, pentaerythritol, trimethylolpropane, ethylenediamine and mixtures thereof.

4. The mask of claim 3, wherein said copolymer is a polyoxyethylene-polyoxypropylene block copolymer wherein said polyoxyethylene moiety constitutes at least about 70% by weight of the copolymer, the average molecular weight of A is at least about 1200, and the total molecular weight of the copolymer is at least about 10,000.

5. The mask of claim 4, wherein the intermediate of Formula II is prepared by initiation with propylene glycol and has a molecular weight of at least about 1500.

6. The mask of claim 3, wherein said polyoxyalkylene block copolymer has the formula

$$HO(C_2H_4O)_b(C_4H_8O)_a(C_2H_4O)_bH \qquad (III)$$

wherein a and b are integers such that the hydrophobe base represented by $(C_4H_8O)_a$ has a molecular weight of at least about 500 as determined by hydroxyl number, the polyoxyethylene chain constitutes at least about 70% by weight of the polyoxyalkylene block copolymer, and the polyoxyalkylene block copolymer has a total average molecular weight of at least 5000; or has the formula

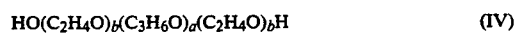
$$HO(C_2H_4O)_b(C_3H_6O)_a(C_2H_4O)_bH \qquad (IV)$$

wherein a and b are integers such that the hydrophobe base represented by $(C_3H_6O)_a$ has an average molecular weight of at least about 900; as determined by hydroxyl number, the polyoxyethylene chain constitutes at least about 70% by weight of the polyoxyalkylene block copolymer, and the polyoxyalkylene block copolymer has a total average molecular weight of at least about 5000; or has the formula

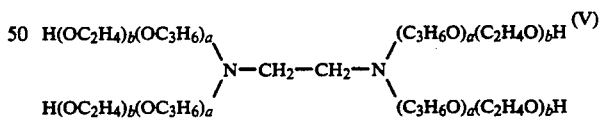

wherein a and b are integers such that the polyoxyalkylene block copolymer has a hydrophobe molecular weight of at least 1500, a hydrophile content of at least about 70% by weight, and a total average molecular weight of at least about 5000.

7. The mask of claim 6, wherein said polyoxyalkylene block copolymer is

present in the amount of about 10% to about 40% by weight of the total weight of said thermally reversible aqueous gel and wherein the counter-ion is present in said thermally reversible aqueous gel in latent form.

8. The mask of claim 7, wherein said polyoxyalkylene block copolymer is present in the amount of about 15% to about 30% by weight in said thermally reversible aqueous gel, said counter-ion is selected from the group consisting of calcium, strontium, aluminum, and mixtures thereof and said ionic polysaccharide is selected from the group consisting of an ammonium alginate, an alkali metal alginate, and mixtures thereof.

9. The mask of claim 7, wherein said polyoxyalkylene block copolymer is present in the amount of about 15% to 30% by weight of said aqueous thermally reversible gel, the latent form of said counter-ion is present as an ionic compound in a microencapsulated component or present as an anion in an ion exchange resin wherein said ionic compound is selected from the group consisting of the metal phosphates, metaphosphates, pyrophosphates, tripolyphosphates, and mixtures thereof, and said ionic polysaccharide is chitosan.

10. A process for excimer laser keratectomy for correction of myopia and hyperopia comprising:
    forming a thermo-reversible aqueous gel corneal mask in situ on a cornea of an eye of a mammal, said mask comprising an aqueous composition having a buffered pH and characterized as a liquid at room temperature or below and a thermo-reversible, osmotically balanced aqueous gel at mammalian body temperature,
    rendering said mask thermo-irreversible by contacting said mask with a divalent or trivalent counter-ion,
wherein said aqueous composition comprises:
    (1) about 0.2% to about 2.5% by weight of an ionic polysaccharide;
    (2) about 10% to about 50% by weight of a polyoxyalkylene block copolymer of formula $$Y[(A)_n-E-H]_x \qquad \text{(I)}$$

wherein A is a polyoxyalkylene moiety having an oxygen/carbon atom ratio of less than 0.5, x is at least 2, Y is derived from water or an organic compound containing x reactive hydrogen atoms, E is a polyoxyethylene moiety, n has a value such that the average molecular weight of A is at least about 500, as determined by the hydroxyl number of an intermediate of formula $$Y[(A)_n-H]_x, \qquad \text{(II)}$$

and the total average molecular weight of the polyoxyalkylene block copolymer is at least about 5000; and
    (3) a pharmaceutically acceptable buffer sufficient to maintain the pH of said aqueous composition at a desired level;
wherein the divalent or trivalent counter-ion is capable of thermo-irreversibly gelling said aqueous composition.

11. The process of claim 10, wherein Y in said formulas I and II is a water soluble organic compound having 1-6 carbon atoms, and said copolymer is selected from the group consisting of a polyoxyethylene-polyoxybutylene block copolymer, a polyoxyethylene-polyoxypropylene block copolymer and mixtures thereof, and wherein the polyoxyethylene moiety constitutes at least 70% by weight of the polyoxyalkylene block copolymer and wherein the pH is maintained at about 7.4±0.2.

12. The process of claim 11, wherein said copolymer is selected from block copolymers which form aqueous gels at a concentration of about 10–40% by weight of the total weight of said composition.

13. The process of claim 12, wherein said Y is a compound selected from the group consisting of propylene glycol, glycerin, pentaerythritol, trimethylolpropane, ethylenediamine, and mixtures thereof.

14. The process of claim 13, wherein Y is derived from propylene glycol, A is the residue of propylene oxide, and the intermediate of Formula II has an average molecular weight of at least about 900.

15. The process of claim 13, wherein Y is derived from butylene glycol, A is the residue of butylene oxide, and the intermediate of Formula II has an average molecular weight of at least about 500

16. The process of claim 13, wherein said excimer laser is an argon fluoride laser which delivers light at about 193 nm and wherein said polyoxyalkylene block copolymer has the formula $$HO(C_2H_4O)_b(C_4H_8O)_a(C_2H_4O)_bH \qquad \text{(III)}$$

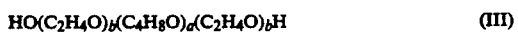

wherein a and b are integers such that the hydrophobe base represented by $(C_4H_8O)_a$ has a molecular weight of at least about 1000, as determined by hydroxyl number, the polyoxyethylene chain constitutes at least about 60% by weight of the polyoxyalkylene block copolymer, and the polyoxyalkylene block copolymer has a total average molecular weight of at least 5,000; or has the formula $$HO(C_2H_4O)_b(C_3H_6O)_a(C_2H_4O)_bH \qquad \text{(IV)}$$

wherein a and b are integers such that the hydrophobe base represented by $(C_3H_6O)_a$ has an average molecular weight of at least about 1500, as determined by hydroxyl number, the polyoxyethylene chain constitutes at least about 60% by weight of the polyoxyalkylene block copolymer, and the polyoxyalkylene block copolymer has a total average molecular weight of at least about 5,000; or has the formula

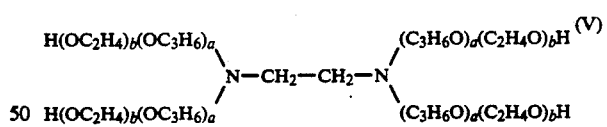

$$\begin{array}{c} H(OC_2H_4)_b(OC_3H_6)_a \\ \phantom{H(OC_2H_4)_b(OC_3H_6)_a} \diagdown \\ N-CH_2-CH_2-N \\ \phantom{H(OC_2H_4)_b(OC_3H_6)_a} \diagup \\ H(OC_2H_4)_b(OC_3H_6)_a \end{array} \begin{array}{c} (C_3H_6O)_a(C_2H_4O)_bH \\ \\ \\ (C_3H_6O)_a(C_2H_4O)_bH \end{array} \qquad \text{(V)}$$

wherein a and b are integers such that the polyoxyalkylene block copolymer has a hydrophobe molecular weight of at least 2000, a hydrophile content of at least about 60% by weight, and a total average molecular weight of at least 5,000.

17. The process of claim 16, wherein said copolymer is

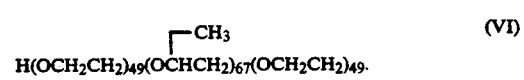

$$H(OCH_2CH_2)_{49}(OCHCH_2)_{67}(OCH_2CH_2)_{49}\text{-} \atop \phantom{H(OCH_2CH_2)_{49}(O}\overset{\displaystyle CH_3}{|}\phantom{CH_2)_{67}(OCH_2CH_2)_{49}\text{-}} \qquad \text{(VI)}$$

18. The process of claim 16, wherein said ionic polysaccharide is chitosan and said counter-ion is present as an ionic compound in a microencapsulated component or present as an anion in an ion exchange resin, wherein said ionic compound is selected from the group consisting of the metal phosphates, metaphosphates, pyrophosphates, tripolyphosphates, and mixtures thereof.

19. The process of claim 16, wherein said counter-ion is selected from the group consisting of calcium, strontium, aluminum, and mixtures thereof, said ionic polysaccharides is selected from the group consisting of an ammonium alginate, an alkali metal alginate, and mixtures thereof, and said counter-ion is present in an ionic compound as a microencapsulated component or present as a cation in an ion exchange resin.

20. A process for excimer laser keratectomy to correct myopia and hyperopia comprising:
    forming a thermally reversible, osmotically balanced aqueous gel composition in situ on a cornea of an eye of a mammal, and
    rendering said composition thermally irreversible by contacting said composition with a divalent or trivalent metal counter-ion,
    said composition having a buffered pH and comprising
    (1) about 0.2% to about 2.5% by weight of an ionic polysaccharide,
    (2) about 0.1% to about 10% by weight of a combination of a surfactant and a polyoxyalkylene polyether having an average molecular weight of about 10,000 to about 100,000, wherein said polyoxyalkylene polyether is selected from the group consisting of
    (A) polyoxyalkylene polyethers prepared by reacting ethylene oxide and at least one lower alkylene oxide having 3 to 4 carbon atoms with at least one active hydrogen-containing compound having from 3 to 10 carbon atoms and from 3 to 6 active hydrogens to prepare a heteric or block copolymer intermediate and further reacting said copolymer intermediate with at least one alpha-olefin oxide having an average carbon chain length of about 20 to about 45 aliphatic carbon atoms and wherein said alpha-olefin oxide is present in the amount of about 0.3 to 10 percent by weight based upon the total weight of said polyether and
    (B) polyoxyalkylene polyethers prepared by reacting ethylene oxide with at least one active hydrogen-containing compound having from 2 to 10 carbon atoms and from 2 to 6 active hydrogens to prepare a homopolymer intermediate and further reacting said homopolymer intermediate with at least one alpha-olefin oxide having an average carbon chain length of about 20 to 45 aliphatic carbon atoms and wherein said alpha-olefin oxide is present in the amount of about 0.3 to 10 percent by weight based on the total weight of said polyether,
    wherein the divalent or trivalent counter-ion is capable of cross-linking the ionic polysaccharide.

21. The process of claim 20, wherein said polyether is prepared using a heteric copolymer intermediate and wherein the pH is maintained at 7.4±0.2.

22. The process of claim 21, wherein said polyether is prepared using an alpha-olefin oxide having an average carbon chain length of about 20 to 30 carbon atoms, present in the amount of about 0.3 to 10 percent of the total weight of said polyether.

23. The process of claim 22, wherein said polyether contains a proportion of ethylene oxide residue to the residue of said lower alkylene oxide of about 70 to about 90 percent by weight of ethylene oxide residue to about 30 to about 10 percent by weight of said lower alkylene oxide residue.

24. The process of claim 23, wherein said polyether is prepared using propylene oxide as the lower alkylene oxide.

25. The process of claim 20, wherein said polyether is prepared using a block copolymer intermediate.

26. The process of claim 25, wherein said polyether is prepared using an alpha-olefin oxide having an average carbon chain length of about 20 to 30 carbon atoms, which is present in the amount of about 0.3 to 10 percent of the total weight of said polyether.

27. The process of claim 26, wherein said polyether is prepared using a proportion of ethylene oxide residue to the residue of said lower alkylene oxide of from about 70 to about 90 percent by weight of ethylene oxide residue to about 30 to about 10 percent by weight of said lower alkylene oxide residue.

28. The process of claim 27, wherein said polyether is prepared using propylene oxide as the alkylene oxide and wherein said excimer laser is an argon fluoride laser which delivers light at 193 nm.

29. The process of claim 20, wherein said polyether is polyether (B).

30. The process of claim 29, wherein said polyether is prepared using an alpha-olefin oxide having an average carbon chain length of about 20 to 30 carbon atoms, present in the amount of about 0.3 to 10 percent of the total weight of said polyether, said ionic polysaccharide is chitosan, and said counter-ion is present as an ionic compound in a microencapsulated component or present as an anion in an ion exchange resin, wherein said ionic compound is selected from the group consisting of the metal phosphates, metaphosphates, pyrophosphates, tripolyphosphates, and mixtures thereof.

31. The process of claim 29, wherein said polyether is prepared using an alpha-olefin oxide having an average carbon chain length of about 20 to 30 carbon atoms, present in the amount of about 0.3 to 10 percent of the total weight of said polyether, said counter-ion is selected from the group consisting of calcium, strontium, aluminum, and mixtures thereof, said ionic polysaccharide is selected from the group consisting of an ammonium alginate, an alkali metal alginate, and mixtures thereof, and said counter-ion is present in an ionic compound as a microencapsulated component or present as a cation in an ion exchange resin.

32. A thermally irreversible, osmotically balanced gel ablatable corneal mask for use in excimer laser keratectomy for correction of myopia and hyperopia, said mask being rendered thermally irreversible, subsequent to corneal contact, with a divalent or trivalent metal counter-ion, said mask being formed from an aqueous composition having a buffered pH and comprising
    (1) about 0.2% to about 2.5% by weight of an ionic polysaccharide, and
    (2) about 0.1% to about 10% by weight of a combination of a surfactant and a polyoxyalkylene polyether having a molecular weight of about 10,000 to about 100,000 which is selected from the group consisting of
    (A) polyoxyalkylene polyethers prepared by reacting ethylene oxide and at least one lower alkylene oxide having 3 to 4 carbon atoms with at least one active hydrogen-containing compound having from 3 to 10 carbon atoms and from 3 to 6 active hydrogens to prepare a heteric or block copolymer intermediate and further reacting said copolymer intermediate with at least one alpha-olefin oxide having an average carbon chain length of about 20 to about 45 aliphatic carbon atoms, and wherein said alpha-olefin oxide is present in the amount of about 0.3 to 10 percent by weight based upon the total weight of said polyether and (B) polyoxyalkylene polyethers prepared by reacting ethylene oxide with at least one active hydrogen-containing compound having from 2 to 10 carbon atoms and from 2 to 6 active hydrogens to prepare a homopolymer intermediate and further reacting said homopolymer intermediate with at least one alpha-olefin oxide having an average carbon chain length of about 20 to 45 aliphatic carbon atoms, and wherein said alpha-olefin oxide is present in the amount of about 0.3 to 10 percent by weight based on the total weight of said polyether, wherein the divalent or trivalent counter-ion is capable of cross-linking the ionic polysaccharide.

33. The mask of claim 32, wherein said polyether is prepared using a heteric copolymer intermediate and wherein the pH is maintained at 7.4±0.2.

34. The mask of claim 33, wherein said polyether is prepared using an alpha-olefin oxide having an average carbon chain length of about 20 to 30 carbon atoms, present in the amount of about 0.3 to 10 percent of the total weight of said polyether.

35. The mask of claim 34, wherein the polyether is prepared using a proportion of ethylene oxide residue to the residue of said lower alkylene oxide of about 70 to about 90 percent by weight of ethylene oxide residue to about 30 to about 10 percent by weight of said lower alkylene oxide residue.

36. The mask of claim 35, wherein said polyether is prepared using propylene oxide as the lower alkylene oxide.

37. The mask of claim 32, wherein said polyether is prepared using a block copolymer intermediate.

38. The mask of claim 37, wherein said polyether is prepared using an alpha-olefin oxide having an average carbon chain length of about 20 to 30 carbon atoms and is present in the amount of about 0.3 to 10 percent of the total weight of said polyether.

39. The mask of claim 38, wherein the polyether is prepared using a proportion of ethylene oxide residue to the residue of said lower alkylene oxide of about 70 to about 90 percent by weight of ethylene oxide residue to about 30 to about 10 percent by weight of said lower alkylene oxide residue.

40. The mask of claim 39, wherein said polyether is prepared using propylene oxide as the lower alkylene oxide.

41. The mask of claim 32, wherein said polyether is polyether (B) of claim 30.

42. The composition of claim 41, wherein said polyether is prepared using an alpha-olefin oxide having an average carbon chain length of about 20 to 30 carbon atoms, present in the amount of about 0.3 to 10 percent of the total weight of said polyether, said counter-ion is selected from the group consisting of calcium, strontium, aluminum, and mixtures thereof, said ionic polysaccharide is selected from the group consisting of an ammonium alginate, an alkali metal alginate, and mixtures thereof, and said counter-ion is present in an ionic compound as a microencapsulated component or present as a cation in an ion exchange resin.

43. The mask of claim 41, wherein said polyether is prepared using an alpha-olefin oxide having an average carbon chain length of about 20 to 30 carbon atoms, present in the amount of about 0.3 to 10 percent of the total weight of said polyether, said ionic polysaccharide is chitosan, and said counter-ion is present as an ionic compound in a microencapsulated component or present as an ionic in an ion exchange resin, wherein said ionic compound is selected from the group consisting of metal phosphates, metaphosphates, pyrophosphates, tripolyphosphates, and mixtures thereof.

44. An ablatable corneal mask for use in excimer laser keratectomy for correction of myopia and hyperopia, said mask comprising a thermally irreversible, osmotically balanced, aqueous gel, having a buffered pH, which is the reaction product of a thermally reversible aqueous gel which is a liquid at room temperature or below and a divalent or trivalent counter-ion, said thermally reversible aqueous gel comprising (1) about 0.2% to about 2.5% by weight of an ionic polysaccharide and (2) about 10% to about 50% by weight of a polyoxyalkylene block copolymer of formula $$Y[(A)_n-E-H]_x \qquad (I)$$

wherein A is a polyoxyalkylene moiety having an oxygen/carbon atom ratio of less than 0.5, x is at least 2, Y is derived from water or an organic compound containing x reactive hydrogen atoms, E is a polyoxyethylene moiety constituting at least 60% by weight of the copolymer, n has value such that the average molecular weight is at least about 500, as determined by the hydroxyl number of an intermediate of formula $$Y[(A)_n-H]_x \qquad (II)$$

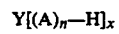

and the total average molecular weight of the copolymer is at least about 5000;

wherein the divalent or trivalent counter-ion is capable of thermo-irreversibly gelling the ionic polysaccharide.

45. A process for excimer laser keratectomy for correction of myopia and hyperopia comprising:

forming a thermo-reversible, osmotically balanced, aqueous gel corneal mask in situ on a cornea of an eye of a mammal, said corneal mask having a buffered pH, and characterized as liquid at room temperature or below and a thermo-reversible gel at mammalian body temperature, and rendering said corneal mask thermo-irreversible by contacting said thermo-reversible corneal mask with a divalent or trivalent metal counter-ion, wherein said thermo-reversible corneal mask is formed using a composition comprising (1) about 0.2% to about 2.5% by weight of an ionic polysaccharide and (2) about 10% to about 50% by weight of a polyoxyalkylene block copolymer of formula $$Y[(A)_n-E-H]_x \qquad (I)$$

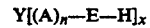

wherein A is a polyoxyalkylene moiety having an oxygen/carbon atom ratio of less than 0.5, x is at least 2, Y is derived from water or an organic compound containing x reactive hydrogen atoms, E is a polyoxyethylene moiety, n has value such that the average molecular weight of A is at least about 500, as determined by the hydroxyl number of an intermediate of formula $$Y[(A)_n\text{—}H]_x \qquad (II)$$

and wherein the total average molecular weight of the polyoxyalkylene block copolymer is at least about 5000;

wherein the divalent or trivalent metal counter-ion is capable of thermo-irreversibly gelling said composition.

* * * * *

UNITED STATES PATENT AND TRADEMARK OFFICE
CERTIFICATE OF CORRECTION

PATENT NO. : 5,277,911
DATED : January 11, 1994
INVENTOR(S) : Viegas et al.

It is certified that error appears in the above-indentified patent and that said Letters Patent is hereby corrected as shown below:

On the title page, under "OTHER PUBLICATIONS", the word "surgery" should be --Surgery--

Column 2, line 39 the word "Arch. Ophthalmol." should be in italics

Column 4, Line 51, the word "Polypnase" should be --Polyphase--

Column 6, Lines 60, 61, and 62, please delete "n has a value such that the average molecular weight of A is at least about 500 to about 900" and replace it with"

Column 8, line 24 after the word "obtained" please add --.--

Column 12, line 60 the word "opthalmic" should be --ophthalmic--

Column 15, line 64, the word "muiltivalent" should be --multivalent--

Column 19, lines 5 and 6, the word "polysaccharides" should be --polysaccharide--

Column 22, line 4, the word "ionic" should be --anion--

Signed and Sealed this

Seventh Day of February, 1995

Attest:

BRUCE LEHMAN

Attesting Officer

Commissioner of Patents and Trademarks